(12) United States Patent
Randhawa et al.

(10) Patent No.: US 11,969,172 B2
(45) Date of Patent: Apr. 30, 2024

(54) HEMOSTASIS RELOADABLE CLIPPING DEVICE WITH SLEEVE ENGAGEMENT

(71) Applicant: BOSTON SCIENTIFIC LIMITED, Hamilton (BM)

(72) Inventors: Nishant Randhawa, S.A.S. Nagar (IN); Sukhvinder Singh, New Delhi (IN); Subodh Morey, Ponda (IN); Federico Rivera, Tres Rios (CR)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 588 days.

(21) Appl. No.: 17/302,305

(22) Filed: Apr. 29, 2021

(65) Prior Publication Data
US 2021/0244418 A1   Aug. 12, 2021

Related U.S. Application Data

(63) Continuation of application No. 15/680,062, filed on Aug. 17, 2017, now Pat. No. 11,020,125.
(Continued)

(51) Int. Cl.
*A61B 17/08* (2006.01)
*A61B 17/122* (2006.01)
(Continued)

(52) U.S. Cl.
CPC ........ *A61B 17/1222* (2013.01); *A61B 17/122* (2013.01); *A61B 17/1285* (2013.01);
(Continued)

(58) Field of Classification Search
CPC ..... A61B 17/1285; A61B 17/12; A61B 17/08; A61B 17/1227; A61B 17/122; A61B 2017/12004; A61B 2090/034
See application file for complete search history.

(56) References Cited

U.S. PATENT DOCUMENTS

2005/0107809 A1* 5/2005 Litscher ............. A61B 17/1285
606/142
2011/0245770 A1* 10/2011 Carrel .................. A61M 5/46
604/117
(Continued)

FOREIGN PATENT DOCUMENTS

CN        103519865     1/2014
JP        2009-011769   1/2009
(Continued)

*Primary Examiner* — Diane D Yabut
*Assistant Examiner* — Christina C Lauer
(74) *Attorney, Agent, or Firm* — Fay Kaplun & Marcin, LLP

(57) ABSTRACT

A system for treating tissue including a clip assembly including a pair of clip arms, a proximal end of each of the clip arms slidably received within a channel of a capsule and moveable between a tissue receiving configuration and a tissue clipping configuration. The system also including an applicator releasably coupleable to the clip assembly, the applicator including a control member connectable to the proximal end of each of the clip arms and a locking sleeve coupleable to a proximal end of the capsule via a deflectable tab including an engaging structure configured to engage a corresponding engaging structure at the proximal end of the capsule and a releasing structure proximal of the engaging structure, the releasing structure engagable with a portion of the control member to deflect the deflectable member and disengage the engaging structure of the locking sleeve from the corresponding engaging structure of the capsule.

13 Claims, 8 Drawing Sheets

Related U.S. Application Data

(60) Provisional application No. 62/378,100, filed on Aug. 22, 2016.

(51) Int. Cl.
*A61B 17/128* (2006.01)
*A61B 17/00* (2006.01)
*A61B 17/12* (2006.01)
*A61B 90/00* (2016.01)

(52) U.S. Cl.
CPC ............... *A61B 2017/00296* (2013.01); *A61B 2017/00477* (2013.01); *A61B 2017/00526* (2013.01); *A61B 2017/0053* (2013.01); *A61B 2017/12004* (2013.01); *A61B 17/1227* (2013.01); *A61B 2090/034* (2016.02)

(56) References Cited

U.S. PATENT DOCUMENTS

| | | |
|---|---|---|
| 2012/0065646 A1 | 3/2012 | Phillips-Hungerford et al. |
| 2013/0304095 A1 | 11/2013 | Barner et al. |

FOREIGN PATENT DOCUMENTS

| | | |
|---|---|---|
| JP | 2009-268637 | 11/2009 |
| JP | 2009-538699 | 11/2009 |
| JP | 2011-206488 | 10/2011 |
| JP | 2012-065835 | 4/2012 |
| JP | 2013-63107 | 4/2013 |
| JP | 2015-043858 | 3/2015 |
| JP | 2015-149997 | 8/2015 |
| JP | 2009-125547 | 6/2019 |
| WO | 2006/062019 | 6/2006 |

\* cited by examiner

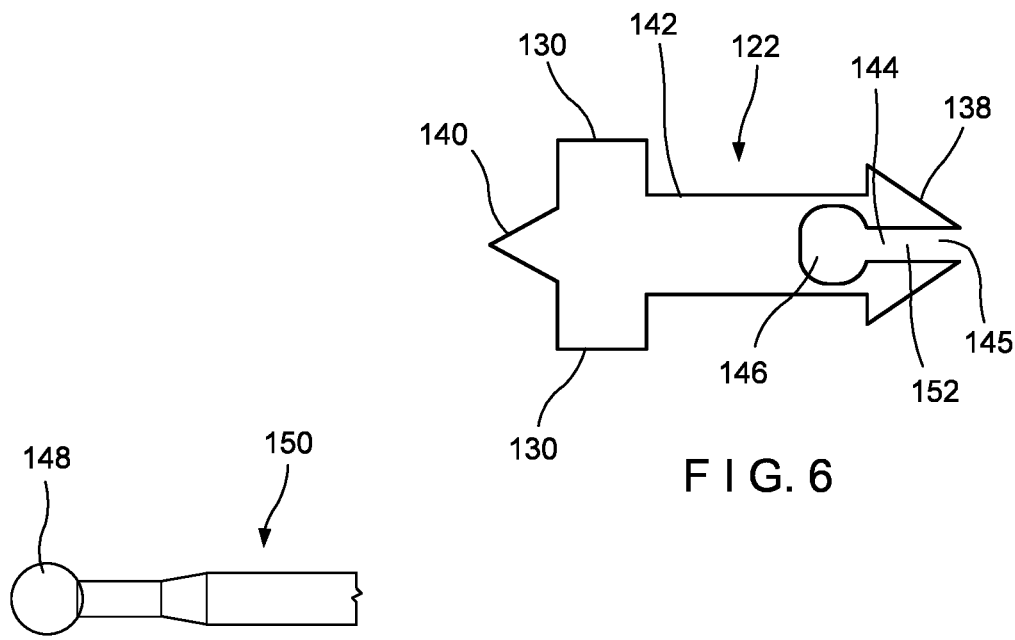
FIG. 6
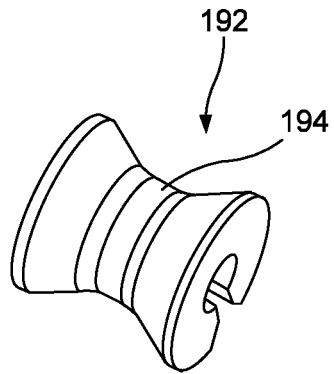
FIG. 7
FIG. 8
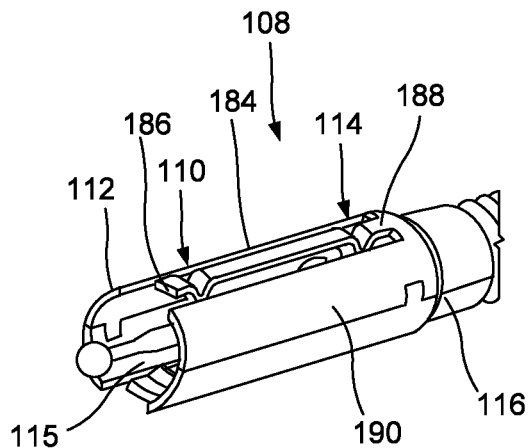
FIG. 9

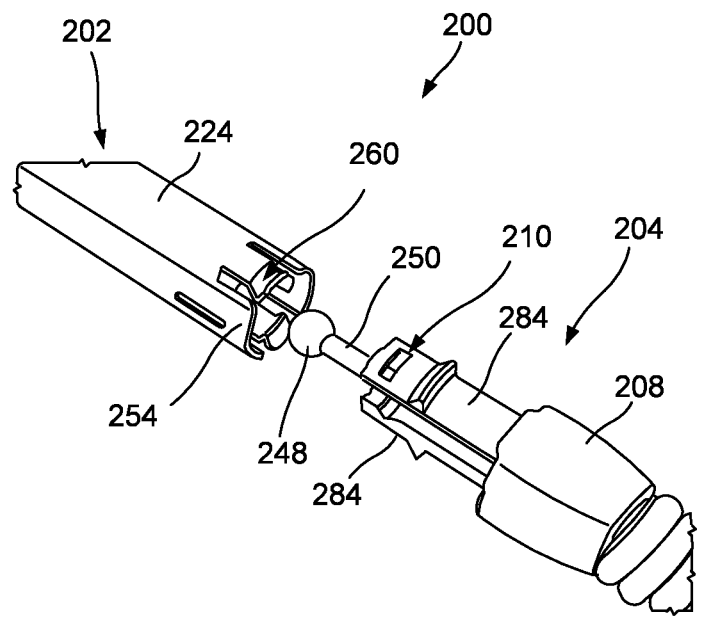
F I G. 13
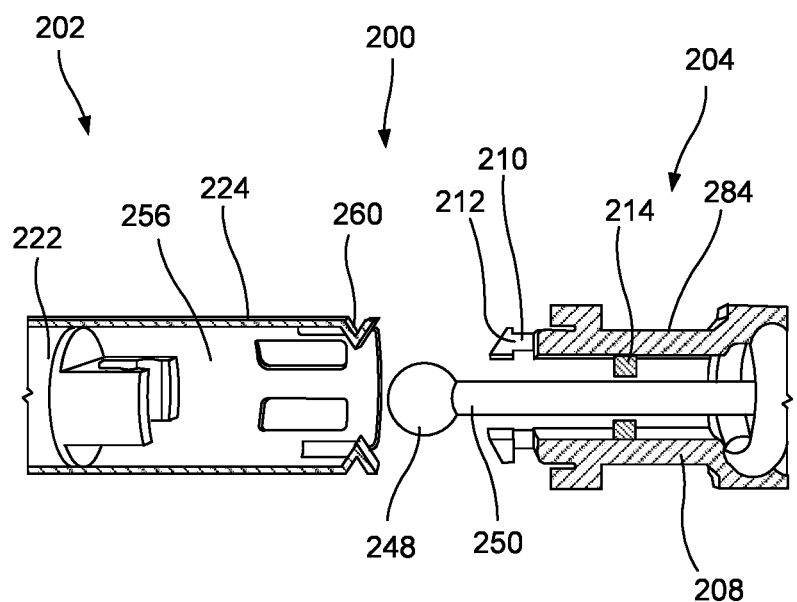
F I G. 14

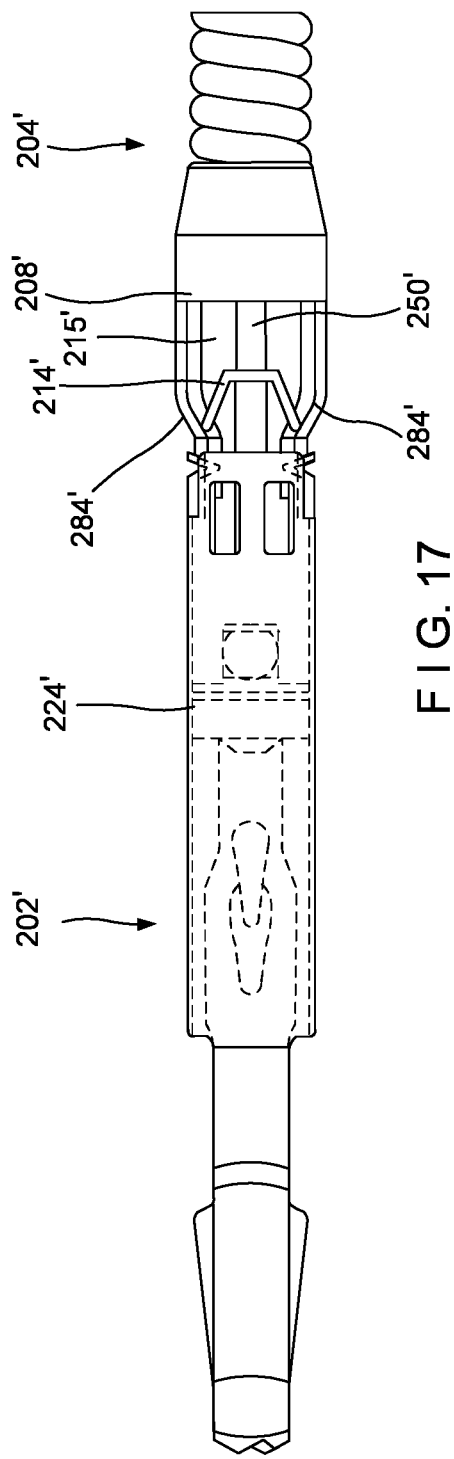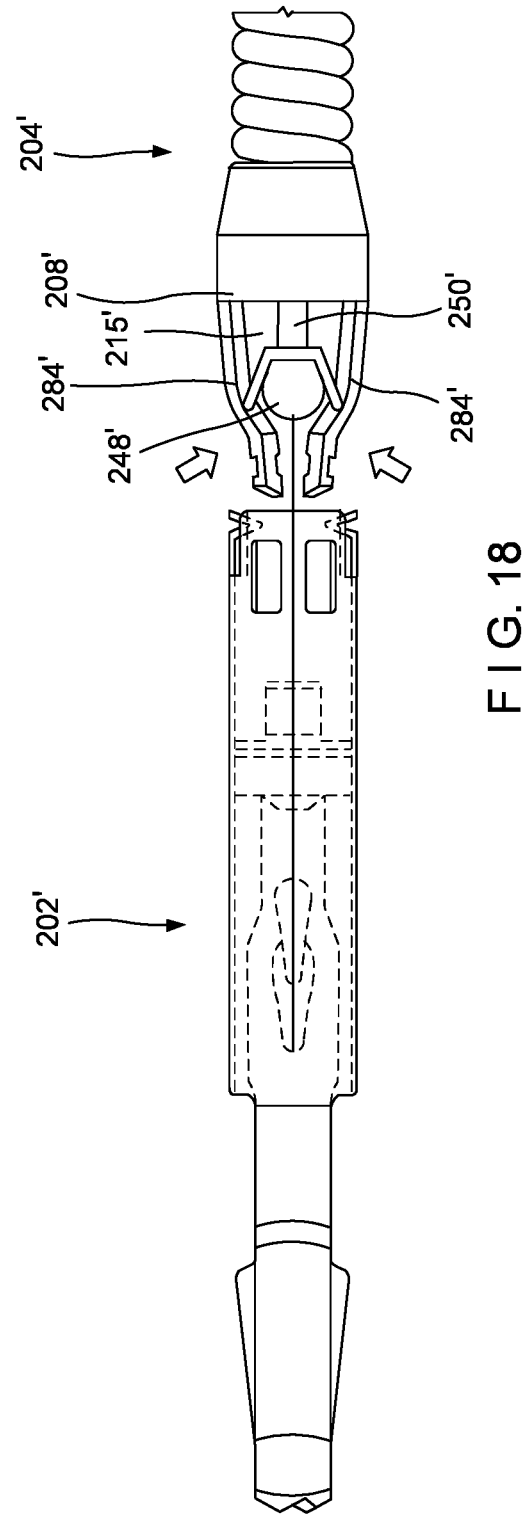

HEMOSTASIS RELOADABLE CLIPPING DEVICE WITH SLEEVE ENGAGEMENT

PRIORITY CLAIM

The present application is a Continuation of U.S. patent application Ser. No. 15/680,062 filed on Aug. 17, 2017; which claims priority to U.S. Provisional Patent Application Ser. No. 62/378,100 filed Aug. 22, 2016; the disclosure of which is incorporated herewith by reference.

BACKGROUND

Pathologies of the gastrointestinal (GI) system, the biliary tree, the vascular system, and other body lumens and hollow organs are often treated through endoscopic procedures, many of which require hemostasis to control internal bleeding. Hemostasis clips grasp tissue surrounding a wound and hold edges of the wound together temporarily to allow natural healing processes to permanently close the wound. Specialized endoscopic clipping devices are used to deliver the clips at the desired locations within the body after which the clip delivery device is withdrawn, leaving the clip within the body.

SUMMARY

The present disclosure relates to a system for treating tissue, comprising a clip assembly and an applicator. The clip assembly includes a pair of clip arms, each of the clip arms extending from a proximal end to a distal end, the proximal end of each of the clip arms being slidably received within a channel of a capsule to be moved between a tissue receiving configuration, in which distal ends of the clip arms are separated from one another, and a tissue clipping configuration, in which distal ends of the clip arms are moved toward one another. The applicator is releasably coupleable to the clip assembly to move the clip assembly between the tissue receiving configuration and the tissue clipping configuration. The applicator includes a control member connectable to the proximal end of each of the clip arms and a locking sleeve coupleable to a proximal end of the capsule via a deflectable tab defined along a length of the locking sleeve from a free distal end to a proximal end connected to the remaining portion of the locking sleeve so that the deflectable tab is deflectable relative to the remaining portion. The deflectable tab includes an engaging structure configured to engage a corresponding engaging structure at the proximal end of the capsule and a releasing structure proximal of the engaging structure, the releasing structure engagable with a portion of the control member to deflect the deflectable member and disengage the engaging structure of the locking sleeve from the corresponding engaging structure of the capsule.

In an embodiment, the engaging structure of the locking sleeve may be a first bend along a distal end of the deflectable tab and the corresponding engaging structure of the capsule may be a window extending laterally therethrough, the window sized and shaped for receiving the first bend.

In an embodiment, the first bend may extend inward into a longitudinal channel of the locking sleeve so that the locking sleeve is mountable over the proximal end of the capsule and the deflectable tab is deflectable away from a longitudinal axis of the channel of the locking sleeve.

In an embodiment, the releasing structure may be a second bend extending into the channel of the locking sleeve.

In an embodiment, the control member may include a body extending longitudinally from an enlarged distal end to a proximal end.

In an embodiment, the proximal ends of the clip arms may be connected via a yoke including a socket sized and shaped for releasably receiving the enlarged distal end of the body of the control member.

In an embodiment, the yoke may be configured to be deformed when a force exerted thereon by the enlarged distal end exceeds a predetermined threshold value.

In an embodiment, the control member may further include a stop washer slidably mounted over a portion of the body, the stop washer including a surface for interfacing with the releasing structure to deflect the deflectable member.

In an embodiment, the engaging structure of the locking sleeve may be a window extending laterally though the deflectable tab and the corresponding engaging structure of the capsule may be a bend extending outward, away from a longitudinal axis of the capsule so that the locking sleeve is receivable within the channel of the capsule and the deflectable tab is deflectable toward a longitudinal axis of the locking sleeve.

In an embodiment, the releasing structure may be a protrusion extending inward into a longitudinal channel of the locking sleeve so that, when a portion of the control tab engages the protrusion, the deflectable tab deflects toward the longitudinal axis of the locking sleeve.

In an embodiment, the releasing structure may be an element extending across a channel of the locking sleeve from an interior surface of the deflectable tab so that, when a portion of the control member engages the releasing structure, the deflectable tab deflects toward the longitudinal axis of the locking sleeve.

In an embodiment, the applicator may further comprise an outer sleeve extending about a portion of the deflectable tab proximal of the engaging structure, the outer sleeve being deformable over the deflectable tab to release the locking sleeve from the capsule.

In an embodiment, the clip arms may be biased in the tissue receiving configuration.

In an embodiment, the capsule may include a locking window extending through a wall thereof for engaging a locking tab at the proximal end of at least one of the clip arms to lock the clip arms in the tissue clipping configuration.

The present disclosure also relates to a reloadable clipping device, comprising a clip assembly, a cartridge and an applicator. The clip assembly includes a pair of clip arms, each of the clip arms extending from a proximal end to a distal end, the proximal end of each of the clip arms connected to one another via a yoke slidably received within a channel of a capsule to move the clip arms between a tissue receiving configuration, in which distal ends of the clip arms are separated from one another, and a tissue clipping configuration, in which distal ends of the clip arms are moved toward one another. The cartridge includes a groove therein, the groove sized and shaped for housing the clip assembly, the cartridge including a proximal opening open to an exterior of the cartridge in communication with the groove. The applicator has a distal portion insertable through the opening of the cartridge to be releasably coupled to the clip assembly, the applicator including a control member having an enlarged distal end sized and shaped to be releasably received within a socket of the yoke and a locking sleeve coupleable to a proximal end of the capsule via a deflectable tab defined along a length of the locking sleeve from a free distal end to a proximal end connected to the remaining portion of the locking sleeve so that the deflectable tab is deflectable away from a longitudinal axis of the locking sleeve, the deflectable tab including a distal bend extending into a channel of the locking sleeve to engage a window extending laterally through the proximal end of the capsule and a proximal bend proximal of the distal bend, the proximal bend extending into the channel of the locking sleeve so that when the proximal bend engages a portion of the control member, the deflectable member is deflected away from the longitudinal axis of the locking sleeve to disengage the applicator from the clip assembly.

The present disclosure also relates to a method for treating tissue, comprising loading a first clip assembly on an applicator by coupling a control member of the applicator to a yoke connecting proximal ends of clip arms of the first clip assembly by pushing an enlarged distal end of the control member into a socket of the yoke, and by coupling a locking sleeve of the applicator to a capsule of the first clip assembly by pushing the locking sleeve distally along the proximal end of the capsule, a deflectable tab of the locking sleeve deflecting such that an engaging structure of the deflectable tab rides along a surface of the capsule until the engaging structure engages a corresponding engaging structure of the capsule, inserting the loaded clip assembly to a target site within a living body via a working channel of an endoscope, moving the first clip assembly between a tissue receiving configuration, in which distal ends of the clip arms are separated from one another, and a tissue clipping configuration, in which distal ends of the clip arms are moved toward one another, by moving the control member longitudinally relative to the locking sleeve until a target tissue is gripped therebetween, as desired, and releasing the first clip assembly from the applicator by drawing the control member proximally relative to the yoke, beyond a predetermined threshold value, so that the control member disengages from the yoke and a portion of the control member engages a releasing structure positioned proximally of the engaging structure on the deflectable tab, engagement of the portion of the control member and the releasing structure causing the deflectable tab to deflect and disengage the engaging structure of the locking sleeve from the corresponding engaging feature of the capsule.

BRIEF DISCLOSURE

FIG. 6 shows a longitudinal side view of a yoke according to the system of FIG. 1;

FIG. 7 shows a longitudinal side view of a distal portion of a control member according to the system of FIG. 1;

FIG. 8 shows a perspective view of a stop washer according to the system of FIG. 1;

FIG. 9 shows a perspective view of a locking sleeve according to the system of FIG. 1;

FIG. 13 shows a perspective view of a clip assembly and an applicator of a system according to another exemplary embodiment of the present disclosure, in an uncoupled configuration;

FIG. 14 shows a longitudinal cross-sectional view of the clip assembly and the applicator of the system of FIG. 13, in the uncoupled configuration;

FIG. 17 shows a longitudinal side view of a system according to an alternate embodiment of the present disclosure;

FIG. 18 shows another longitudinal side view of the system of FIG. 17;

DETAILED DESCRIPTION

Figure 1:
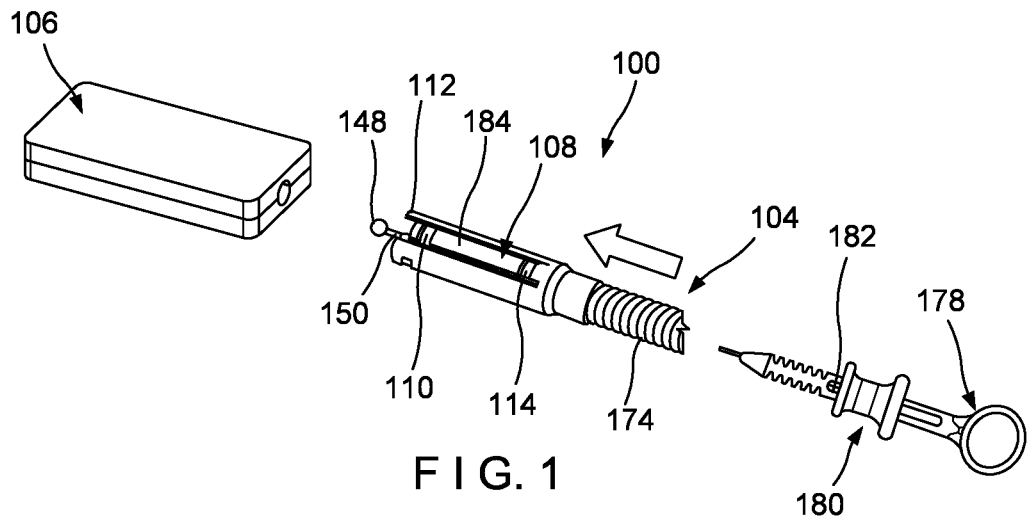
FIG. 1 shows a perspective view of a system according to an exemplary embodiment of the present disclosure, in an unassembled configuration.

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to an endoscopic procedure. Once a clip has been deployed at a desired target area in the body, the applicator assembly may be reloaded with a new clip. In particular, the applicator assembly includes a locking sleeve for releasably engaging the clip assembly. The locking sleeve may include a releasing structure facilitating engagement with the clip assembly and a releasing structure facilitating release of the clip assembly from the applicator assembly. It should be noted that the terms "proximal" and "distal," as used herein, are intended to refer to a direction toward (proximal) and away from (distal) a user of the device.

Figure 2:
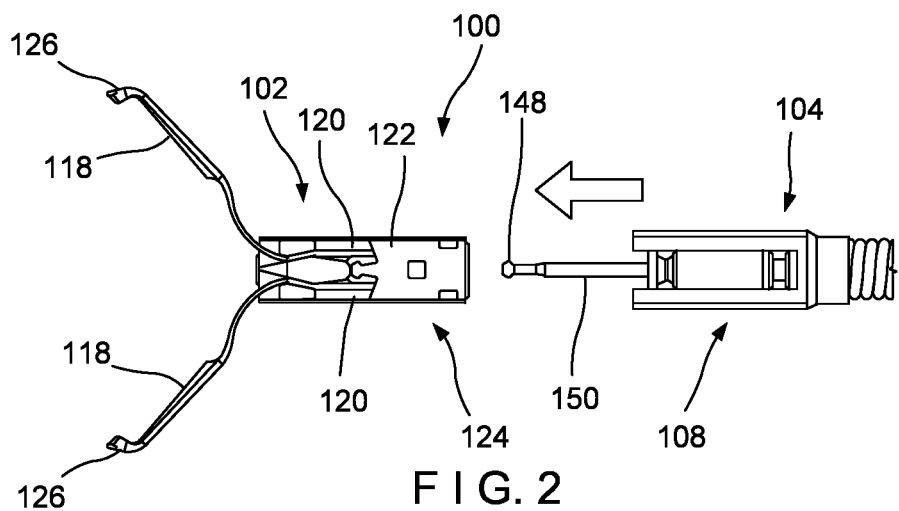
FIG. 2 shows a longitudinal side view of the system of FIG. 1, in the unassembled configuration.
Figure 3:
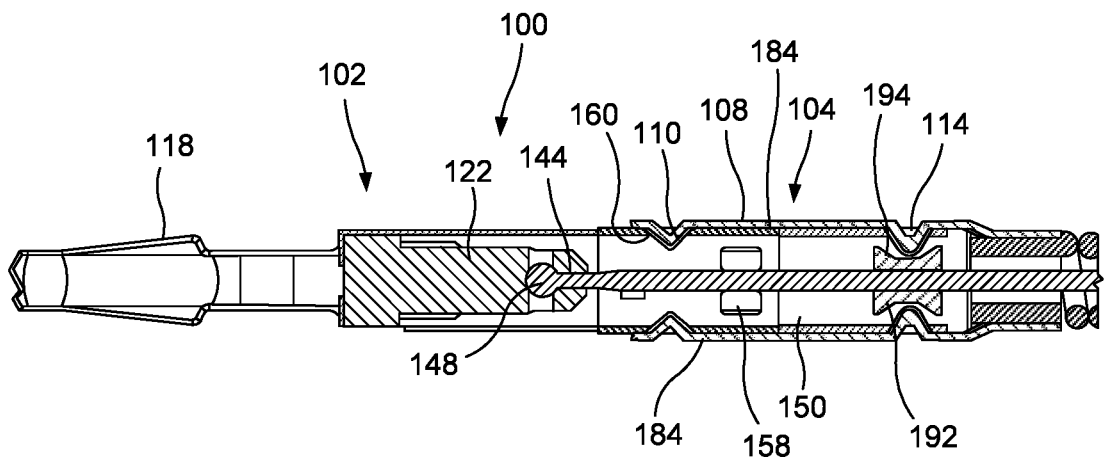
FIG. 3 shows a longitudinal cross-sectional view of the system of FIG. 1, in the assembled configuration.
Figure 4:
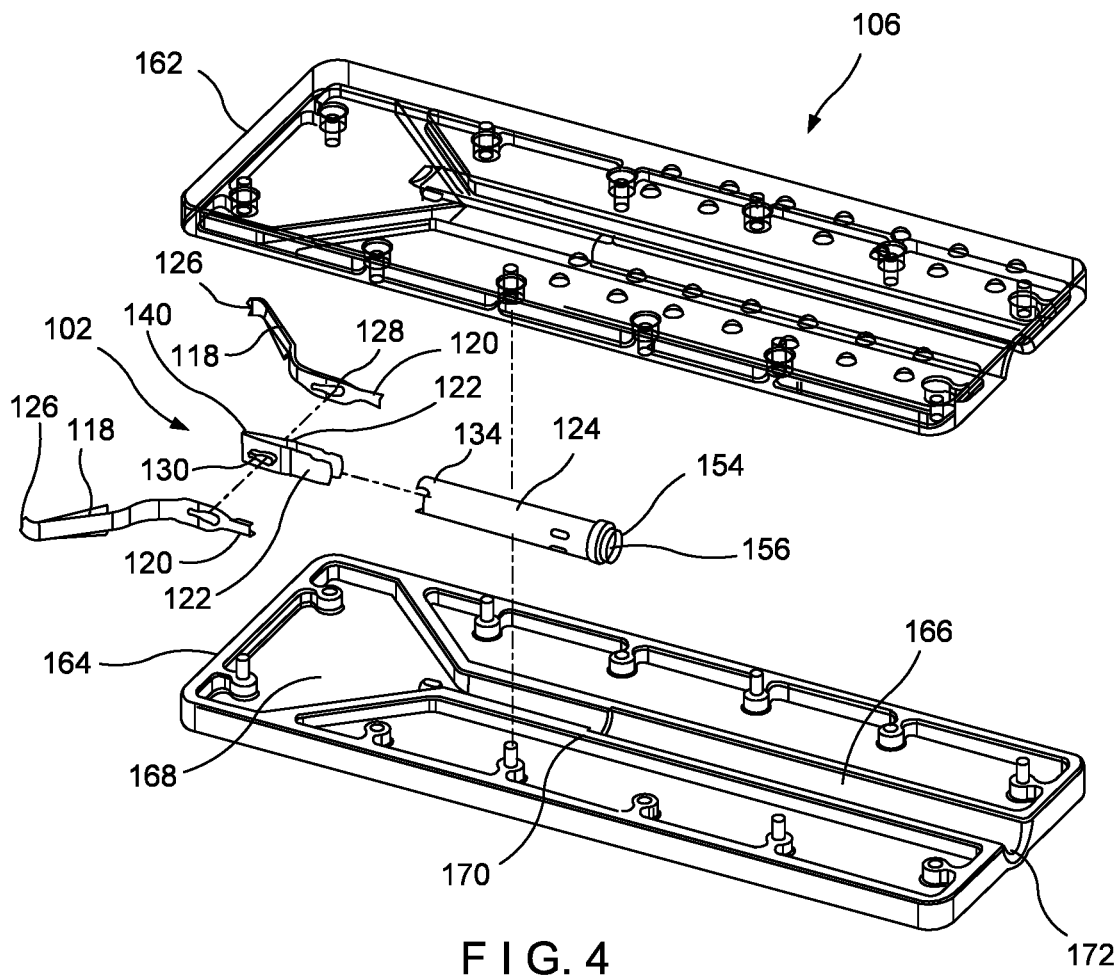
FIG. 4 shows an exploded perspective view of a cartridge and clip assembly of the system of FIG. 1.

As shown in FIGS. 1-12, a system 100 according to an exemplary embodiment of the present disclosure comprises a clip assembly 102, an applicator 104 and a cartridge 106. As shown in FIGS. 1-3, the clip assembly is loadable onto a distal portion of the applicator 104 prior to insertion of the system 100 into a living body for the clipping of target tissue. The applicator 104 is configured such that, after deployment of the clip assembly 102 in the living body, a new clip assembly 102 may be loaded onto the applicator 104 so that the same applicator 104 may be used to deliver a new clip assembly 102 to a second portion of target tissue in the living body. As shown in FIG. 4, each clip assembly 102 according to this embodiment, is stored in a cartridge 106, which facilitates loading of the clip assembly 102 onto the applicator 104. In particular, the applicator 104 includes a locking sleeve 108 at a distal end thereof for releasably engaging the clip assembly 102. As will be described in greater detail below, the locking sleeve 108 includes an engaging structure 110 at a distal end 112 thereof facilitating engagement with the clip assembly 102 and a releasing structure 114 proximal of the engaging structure 110 facilitating release of the clip assembly 102 from the applicator 104.

The clip assembly 102 includes a pair of clip arms 118, proximal ends 120 of are, in this embodiment, connected to one another via a yoke 122 that is slidably received within a capsule 124. The clip arms 118 of this embodiment are biased so that distal ends 126 thereof move apart from one another into a tissue receiving configuration when not drawn into the capsule 124. When drawn into the capsule 124, the capsule 124 constrains the clip arms 118, holding the distal ends 126 thereof together in a tissue clipping configuration. The yoke 122 is longitudinally slidable within the capsule 124 to move the clip arms 118 between the tissue receiving configuration and the tissue clipping configuration.

Figure 5:
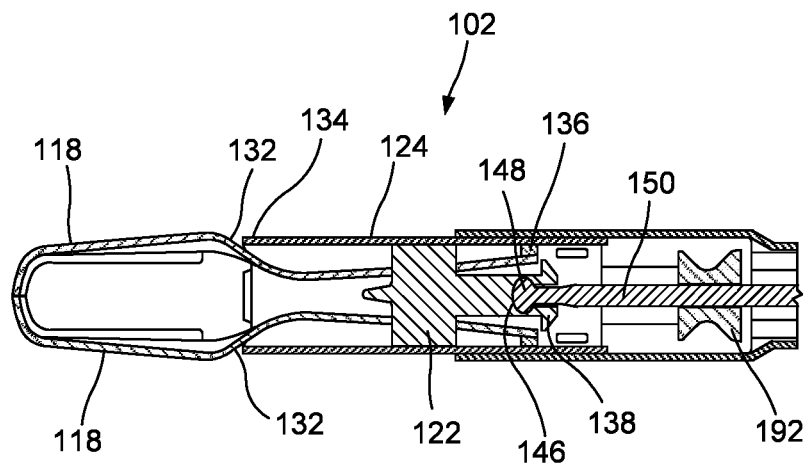
FIG. 5 shows a longitudinal cross-sectional view of the system of FIG. 1, in a tissue clipping configuration.

Each of the clip arms 118 extends from a proximal end 120 to a distal end 126. The distal ends 126 of each of the clip arms 118 in this embodiment projecting laterally inward toward the distal end 126 of the other of the clip arms 118 to facilitate gripping of target tissue therebetween. The distal ends 126 may further include other gripping features such as, for example, teeth and/or protrusions. A proximal portion of each of the clip arms 118 may include an opening 128 sized and shaped to receive therein a corresponding protrusion 130 of the yoke 122 so that the clip arms 118 are engaged and aligned with the yoke 122. Thus, moving the yoke 122 relative to the capsule 124 moves the clip arms 118 proximally and distally relative to the capsule 124, thereby moving the clip arms 118 between the tissue receiving and clipping configurations. As described above, the clip arms 118, according to this embodiment, are biased toward the open configuration and are shaped so that, when the yoke 122 is drawn proximally into the capsule 124, an interior surface of the capsule 124 engages an exterior surface of, for example, a shoulder 132 of the clip arms 118 to draw the clip arms together toward the tissue clipping configuration, as shown in FIG. 5. When the yoke 122 is moved distally relative to the capsule 124, the shoulder 132 of each of the clip arms 118 extends distally beyond a distal end 134 of the capsule 124 freeing the clip arms 118 to move apart from one another under their natural bias toward the tissue receiving configuration.

Each of the proximal ends 120 of the clip arms 118 includes a locking tab 136 extending laterally outward therefrom. The clip arms 118 are biased so that, when the clip arms 118 are being locked in the tissue clipping configuration, the locking tab 136 of each of the clip arms 118 springs outward to lockingly engage a portion of the capsule 124. Engagement of the locking tabs 136 with the capsule 124 locks the clip assembly 102 in the tissue clipping configuration to securely grip any tissue received between the distal ends 126 of the clip arms 118 and prevent the clip arms 118 from being moved proximally out of the capsule 124.

As shown in FIG. 6, the yoke 122 extends longitudinally from a proximal end 138 to a distal end 140 and includes a pair of protrusions 130 extending laterally outward from an exterior surface 142 thereof. Each of the protrusions 130 is sized and shaped to be received within a corresponding one of the openings 128 of the clip arms 118. As described above, receipt of each of the protrusions 130 within the corresponding opening 128 of the clip arms 118 maintains the clip arms 118 in alignment relative to one another, the yoke 122 and the capsule 124. The yoke 122 further includes a longitudinal slot 144 extending from a proximal opening 145 at the proximal end 138 of the yoke 122 along a longitudinal axis of the yoke 122 to a distal portion 146 which is sized and shaped to receive an enlarged end 148 of a control member 150 of the applicator 104. In one exemplary embodiment, as shown in FIG. 7, the enlarged end 148 may be configured as a ball which is received within a correspondingly sized and shaped socket of the distal portion 146. A proximal portion 152 of the slot 144 extending between the proximal opening 145 and the distal portion 146 has a cross-sectional area (e.g., diameter) smaller than a cross-sectional area of the distal portion 146 with opposed portions of the proximal portion 152 being spreadable to receive the enlarged end 148 and biased toward one another so that, once the enlarged end 148 passes distally into the distal portion 146, the opposed portions of the proximal portion 152 spring back to lock the enlarged end within the distal portion 146, coupling the control member 150 to the yoke 122. Thus, longitudinal movement of the control member 150 relative to the capsule 124 may control movement of the clip arms 118 between the tissue receiving and the tissue clipping configurations.

According to this embodiment, the enlarged end 148 of the control member 150 may be inserted into the distal portion 146 via the proximal opening 145 of the yoke 122. When the control member 150 is pushed distally into the yoke 122 beyond a predetermined threshold value, the proximal opening 145 of the slot 144 deforms to permit the enlarged end 148 to be passed through the proximal portion 152 into the distal portion 146. In one embodiment, portions of the yoke 122 defining the slot 144 may be separated from one another to permit the enlarged end 148 to be passed through the proximal portion 152 into the distal portion 146. Once the enlarged end is received within the distal portion 146, the proximal portion 152 of the slot 144 reverts to its original size, holding the enlarged end 148 of the control member 150 in the distal portion 146.

The capsule 124 extends longitudinally from a proximal end 154 to the distal end 134 and includes a channel 156 extending longitudinally therethrough (FIG. 4). The channel 156 is sized and shaped to receive the yoke 122 and a proximal portion of the clip arms 118 therein. The capsule 124 according to this embodiment includes a pair of locking windows 158 (FIG. 10) extending laterally therethrough for engaging the locking tabs 136 of the clip arms 118, to lock the clip arms 118 in the tissue clipping configuration. As described above, the proximal ends 120 of the clip arms 118 are biased outward so that the locking tabs 136 may ride along the interior surface of the capsule 124 until the locking tabs 136 are drawn proximally into alignment with the locking windows 158. The locking windows 158 may be positioned proximate the proximal end 154 of the capsule 124 so that the clip arms 118 may be repeatedly moved between the tissue receiving and clipping configurations until it is desired to lock the clip assembly 102 in the tissue clipping configuration by moving the control wire 150 further proximally so that the locking tabs 136 engage the locking windows 158.

In this embodiment, the capsule 124 further includes engaging windows 160 for engaging a corresponding engaging structure 110 of the locking sleeve 108 of the applicator 104 when the clip assembly 102 is loaded thereon. Each of the engaging windows 160 extends laterally through the capsule 124 and is sized and shaped to receive the engaging structure 110. In one exemplary embodiment, the capsule 124 may include two engaging windows 160 for engaging two engaging structures 110. The capsule 124, however, may include any number of engaging windows 160 for receiving a corresponding number of engaging structures 110. The engaging windows 160 may be offset from the locking windows 158 about a longitudinal axis of the capsule 124 to prevent the locking tabs 136 from inadvertently engaging any portion of the engaging windows 160. In one particular embodiment, the engaging windows 160 may be offset 90° from the locking windows 158. Although the capsule 124 is shown and described as including engaging windows 160 for engaging the engaging structures 110, the capsule 124 may include other engaging structures so long as the engaging structures are capable of engaging the engaging structure 110 upon loading of the clip assembly 102 thereon.

Prior to being loaded on the applicator 104, the clip assembly 102 is stored in a cartridge 106, as shown in FIG. 4, which may be configured, for example, as a storage container comprising a base 162 and a lid 164. The base 162 and the lid 164 include features for coupling the base 162 and the lid 164 to one another so that the clip assembly 102 may be securely stored therein. In one embodiment, each of the base 162 and the lid 164 includes a groove 166 which, when the base 162 and the lid 164 are assembled with one another, forms a space for housing the clip assembly 102. The clip assembly 102 may be stored in the assembled cartridge 106 in the tissue receiving configuration. Thus, the groove 166 may include a distal portion 168 sized and shaped for receiving the clip arms 118 in the tissue receiving configuration (i.e., distal ends 126 separated from one another) and a proximal portion 170 sized and shaped to receive the capsule 124. The proximal portion 170 may include a proximal opening 172 through which the distal portion of the applicator 104 may be inserted into the cartridge 106 to load the clip assembly 102 thereon.

The applicator 104 includes the locking sleeve 108, a flexible member 174 extending proximally therefrom, and the control member 150 extending through the locking sleeve 108 and the flexible member 174. A proximal end of the flexible member 174 is connected to a handle member 178 which includes an actuator such as, for example, a spool 180, coupled thereto. In one example, as shown in FIG. 1, the spool 180 is coupled to a proximal end 182 of the control member 150 so that, once the clip assembly 102 is loaded onto the applicator 104, the spool 180 may be slid longitudinally over the handle member 178 to moves the clip assembly 102 between the tissue receiving and clipping configurations, as described above. Specifically, sliding the spool 180 over the handle member 178 moves the control member 150 relative to the capsule 124, which is engaged to the applicator 104. Thus, the spool 180 may also be moved relative to the handle member 178 to lock the clip assembly 102 in the tissue clipping configuration and to deploy the clip assembly in the living body.

The flexible member 174 may be formed as a coil of wire through which the control member 150 extends from the enlarged distal end 148 to the proximal end 182. As would be understood by those skilled in the art, the coil of wire preferably has sufficient flexibility to be passed through even tortuous paths of living body and, in this embodiment, is sized and shaped to permit it to be passed through a working channel of an endoscope or other insertion device. Although the flexible member 178 is shown and described as a coil of wire, it will be understood by those of skill in the art that any other suitable flexible structure may be employed so long as the flexible member 174 is capable of providing a force in compression sufficient to counter the tension to be placed on the control member 150 from the clip assembly 102. Although the applicator 104 is described as including the spool 180, the applicator 104 may include any of a variety of actuating mechanisms for moving the control member 150 to control movement of the clip arms 118.

As described above, the control member 150 extends from the enlarged distal end 148 releasably coupleable to the yoke 122 to the proximal end 182 connected to the spool 180. A stop washer 192, as shown in greater detail in FIG. 8, is slidably mounted over a length of the control member 150. The stop washer 192 may include an exterior surface sized and shaped for engaging the releasing structure 114 of the locking sleeve 108. For example, an exterior surface of the stop washer 192 may include an angled and/or curved recess 194 sized and shaped to receive at least a portion of the releasing structure 114 therein, as will be described in further detail below.

Figure 10:
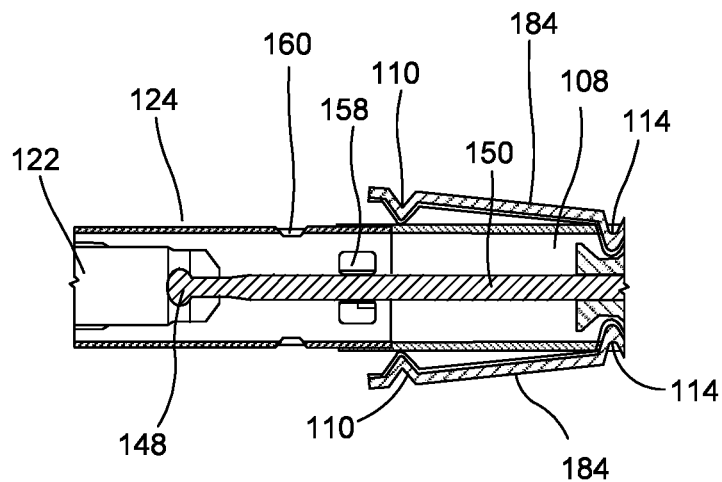
FIG. 10 shows a longitudinal cross-sectional view of a clip assembly and applicator being coupled to one another according to the system of FIG. 1.

As shown in FIG. 9, the locking sleeve 108 extends longitudinally from the distal end 112 to a proximal end 116 and includes a channel 115 extending therethrough. As described above, the locking sleeve 108 includes the engaging structure 110 for connecting the applicator 104 to the clip assembly 102 and the releasing structure 114 for releasing the clip assembly 102 from the applicator 104. Specifically, according to this embodiment, the locking sleeve 108 defines at least one deflectable tab 184 extending longitudinally along a portion thereof, the deflectable tab 184 including the engaging structure 110 and the releasing structure 114. The deflectable tab 184 extends from a free distal end 186 at the distal end 112 of the locking sleeve 108 to a proximal end 188 connected to a remaining portion 190 of the locking sleeve 108 so that the deflectable tab 184 may be deflected away from a longitudinal axis of the locking sleeve 108. For example, the connection between the proximal end 188 and the remaining portion 190 acts as a hinge permitting the distal end 186 of the deflectable tab 184 to be moved away from the longitudinal axis of the locking sleeve 108 so that the deflectable tab 184 is deflected away therefrom, as shown in FIG. 10. In one particular embodiment, the locking sleeve 108 includes two deflectable tabs 184 diametrically opposed from one another. The locking sleeve 108, however, may include any number of deflectable tabs 184 so long as the capsule 124 includes a corresponding number of engaging windows 160 for engaging the engaging structure 110 of each deflectable tab 184.

Figure 11:
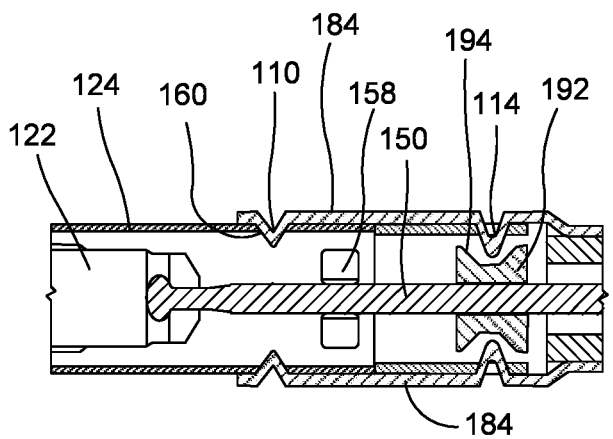
FIG. 11 shows a longitudinal cross-sectional view of the clip assembly and the applicator coupled to one another according to the system of FIG. 1.

The engaging structure 110 of each of the deflectable tabs 184 may, for example, be proximate the distal end 186 thereof while the releasing structure 114 of each of the deflectable tabs 184 is proximate the proximal end 188 thereof. Each of the engaging structure 110 and the releasing structure 114 may be configured as bends along the deflectable member 184. In particular, the bends of the engaging and releasing structures 110, 114 of this embodiment extend into the channel 115 of the locking sleeve 108. The bends of the engaging and releasing structures 110, 114 may be formed as, for example, angled and/or curved surfaces extending into the channel 115. Thus, when the locking sleeve 108 is moved distally over the capsule 124 to be mounted thereover, the proximal end 154 of the capsule 124 engages the engaging structure 110, causing the deflectable member 184 to deflect away from the longitudinal axis of the locking sleeve 108 so that the engaging structure 110 rides along an exterior surface of the capsule 124 until the engaging structure 110 is received within the engaging window 160 of the capsule 124. Receipt of the engaging structure 110 within the engaging window 160 permits the deflectable member 184 to revert to its original, non-deflected configuration to releasably couple the applicator 104 to the clip assembly 102, as shown in FIG. 11.

Prior to engagement of the applicator 104 with the clip assembly 102, the stop washer 192 is positioned within the locking sleeve 108 such that the stop washer 192 engages the releasing structure 114. According to this embodiment, the stop washer 192 is received radially within the locking sleeve 108 so that the recess 194 is aligned and in engagement with the bend of the releasing structure 114. Once the applicator 104 is loaded with the clip assembly 102 and deployment of the clip assembly 102 is desired, the control member 150 is drawn proximally relative to the clip assembly 102 until a force applied by the enlarged end 148 against the slot 144 of the yoke 122 exceeds a threshold force, disengaging the control member 150 from the yoke 122. Upon disengagement of the control member 150 from the yoke 122, the enlarged end 148 comes into contact with a distal end 196 of the stop washer 192, moving the stop washer 192 proximally relative to the locking sleeve 108. As the stop washer 192 is moved proximally relative to the locking sleeve 108, the angled/curved surfaces of the recess 194 interfaces with the angles/curves of the bend of the releasing structure 114 to cause the deflectable member 184 to deflect away from capsule 124. Deflection of the deflecting member 184 causes the engaging structure 110 to be disengaged from the engaging window 160, thereby releasing the clip assembly 102 from the applicator 104 and deploying the clip assembly 102 within the living body.

An exemplary method for loading the clip assembly 102 housed within the cartridge 106 to the applicator 104 comprises inserting the control member 150 and the locking sleeve 108 of the applicator 104 through the proximal opening 172 of the cartridge 106. The enlarged end 148 of the control member 150 is moved with respect to the cartridge 106 by, for example, moving the spool 180 distally relative the handle member 178. The enlarged end 148 is pushed distally against the yoke 122 until a distal force of the enlarged end 148 against the yoke 122 exceeds a predetermined threshold value, deforming the proximal opening 145 of the slot 144 of the yoke 122 to permit the enlarged end 148 to pass therethrough into the distal portion 146 of the slot 144. Once the enlarged end 148 is received within the distal portion 146, the yoke 122 reverts to its original shape, holding the enlarged end 148 therewithin.

Upon coupling the control member 150 to the yoke 122, the locking sleeve 108 is moved distally over the capsule 124, with the deflectable member 184 deflecting away from the longitudinal axis thereof such that the engaging structure 110 rides along the exterior surface of the capsule 124 until the engaging structure 110 is received within the engaging window 160. Once the engaging structure 110 has been received within the engaging window 160, the clip assembly 102 is successfully loaded on the applicator 104. Thus, moving the control member 150 proximally with respect to the cartridge 106 moves the clip assembly 102 from the tissue receiving configuration to the tissue clipping configuration. Once the clip assembly 102 is in the tissue clipping configuration, the entire applicator 104 may be moved proximally relative to the cartridge 106 to draw the clip assembly 102 out of the cartridge via the proximal opening 172.

In use, after the clip assembly 102 has been loaded onto the applicator 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted to the target tissue in the closed configuration to facilitate its passage through the working channel. Upon reaching the site of the target tissue, the clip assembly 102 is advanced out of the distal end of the working channel and the clip arms 118 are extended out of the capsule 124 to move the clip arms 118 to the tissue receiving configuration by, for example, sliding the spool 180 distally over the handle member 178. The clip assembly 102 may be rotated 360° via the handle member to move the clip arms 118 in a desired position over a target portion of tissue. The clip arms 118 may be advanced out of and retracted into the capsule 124 repeatedly to move the clip assembly between the open and the closed configurations until the target portion of tissue is received as desired between the clip arms 118. At this point, the clip arms 118 are moved toward the closed configuration by moving the control member 150 proximally relative to the clip assembly 102. When it is confirmed that the desired portion of tissue is gripped between the clip arms 118 (e.g., portions of tissue on opposite sides of a bleeding wound), the control member 150 is drawn further proximally relative to the clip assembly 102 (via the spool 180) to lock the clip assembly 102 in the closed configuration. That is, the clip arms 118 are drawn further proximally into the capsule 124 until locking tabs 136 at the proximal ends 120 thereof engage the locking windows 158, thereby locking the clip assembly 102 in the tissue clipping configuration.

Figure 12:
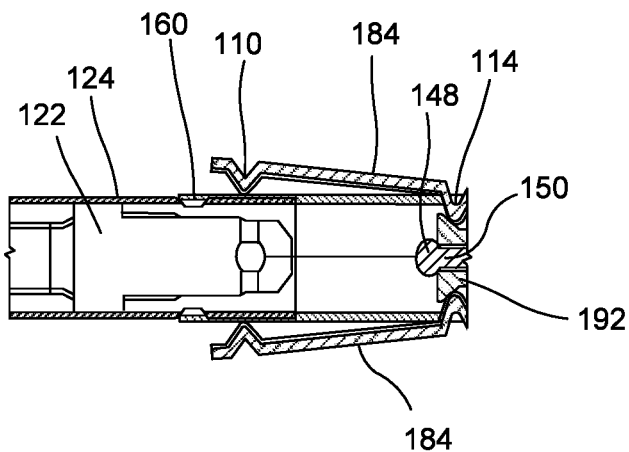
FIG. 12 shows a longitudinal cross-sectional view of the clip assembly being released from the applicator according to the system of FIG. 1.
Figure 15:
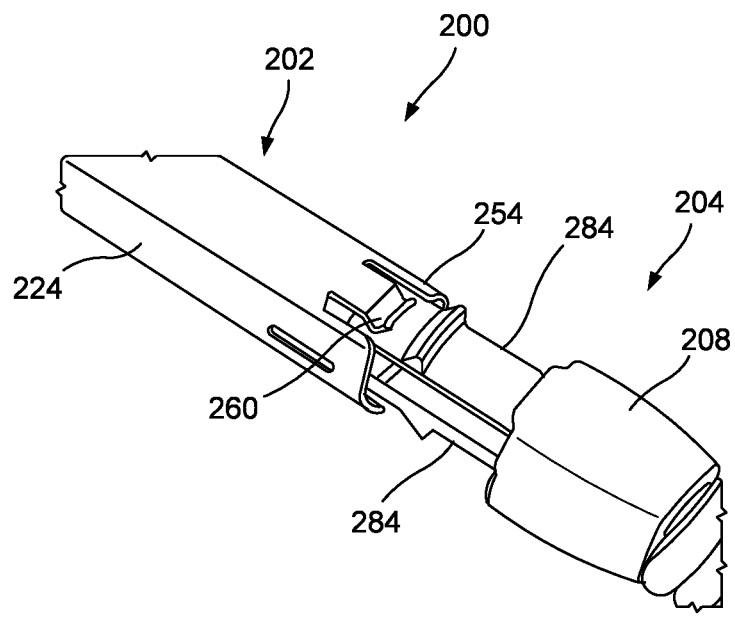
FIG. 15 shows a perspective view of the clip assembly and the application of the system of FIG. 13, in a coupled configuration.

When the clip assembly 102 is locked in the tissue clipping configuration, the clip arms 118 and the yoke 122 are fixed with respect to the capsule 124. Thus, drawing the control member 150 even further proximally relative to the clip assembly 102 exerts a force on the yoke 122. When the enlarge end 148 of the control member 150 exerts a force on the yoke 122 beyond a predetermined threshold value, the yoke 122 deforms (e.g., the proximal opening 145 expands) to permits the enlarged end 148 to be released therefrom. As shown in FIG. 12, once the enlarged end 148 is released from the yoke 122, the enlarged end 148 contacts the stop washer 192, which engages the releasing structure 114 of the locking sleeve 108, and pushes proximally thereagainst so that angles/curves defining the recess 194 interface with angled/curved surface of the releasing structure 114 to once again deflect the deflecting member 184 away from the capsule 124. Deflection of the deflecting member 184 causes the engaging structure 110 to disengage the engaging window 160. The control member 150 is drawn proximally until the locking sleeve 108 is entirely disconnected from the capsule 124, releasing the clip assembly 102 from the applicator 104. The clip assembly 102 is left in the body clipped over the target tissue as the applicator 104 is withdrawn from the body. If so desired, a new clip assembly 102 is then loaded onto the applicator 104, in the same manner as described above, so that the device may then be used to clip a second portion of tissue. This process may be repeated using the same applicator 104 as many times as needed or desired.

Although the exemplary system 100 is shown and described as loading the clip assembly 102 onto the applicator 104 by mounting the locking sleeve 108 over the capsule 124, a clip assembly may also be releasably engaged to an applicator by receiving a portion of the applicator within a proximal opening of the capsule. In addition, although the engaging and releasing structures 110, 114 are shown and described as bends along the deflectable member 184 of the locking sleeve 108, other engaging and releasing structures 110, 114 are possible.

For example, FIGS. 13-16, show a system 200 according to an exemplary embodiment substantially similar to the system 100 described above except as described below. The system 200 comprises a clip assembly 202 loadable on a distal portion of an applicator 204 in the same manner described above except for the differences outlined below. Similarly to the system 100, the clip assembly 202 is housed within a cartridge configured so that a portion of the applicator 204 may be inserted therein to connect (e.g., load) the clip assembly 202 and the applicator 204 to one another. Similarly to the applicator 104, the applicator 204 includes a locking sleeve 208 with an engaging structure 210 for engaging a capsule 224 of the clip assembly 202 and a releasing structure 214 for disengaging the applicator 204 from the clip assembly 202. The applicator 204 and the clip assembly 202 may be releasably coupled to one another substantially as described above with respect to system 100. In particular, a control member 250 of the applicator 204 may be coupled to the yoke 222 substantially as described above with respect to the control member 150 and the yoke 122. The locking sleeve 208, however, is not configured to be mounted over a proximal end 254 of the capsule 224. Rather, a distal end 212 of the locking sleeve 208 is configured to be inserted into the proximal end 254 of the capsule 224 to releasably couple the clip assembly 202 to the applicator 204, as will be described in further detail below.

The clip assembly 202 is substantially similar to the clip assembly 102, described above in regard to the system 100, comprising a pair of arms, proximal ends of which are connected to a yoke 222 slidably received within a capsule 224 to move the arms between tissue receiving and tissue gripping configurations as described above. The capsule 224, however, does not include engaging windows extending laterally through a wall thereof for engaging a portion of the locking sleeve 208 of the applicator 204. Rather, the proximal end 254 of the capsule 224 defines a bend 260 or other engaging feature extending into a channel 256 of the capsule 224, with the bend 260 sized and shaped to engage the engaging structure 210 of the locking sleeve 208.

The engaging structure 210 of this embodiment is configured as a window extending laterally through a distal portion of a deflectable tab 284 of the locking sleeve 208. The window of the engaging structure 210 may be sized and shaped to receive the bend 260 of the capsule 224 when the locking sleeve 208 is inserted into the proximal end 254 of the capsule. As the locking sleeve 208 is inserted into the capsule 224, the deflectable tab 284 of the locking sleeve 208 extends inward, toward a longitudinal axis of the locking sleeve 208, until the bend 260 of the capsule 224 is received within the engaging structure 210 (e.g., window) of the locking sleeve 208. Once the bend 260 is received within the engaging structure 210, the deflectable tab 284 may revert to its original position, engaging the capsule 224 and the locking sleeve 208 to one another.

Figure 16:
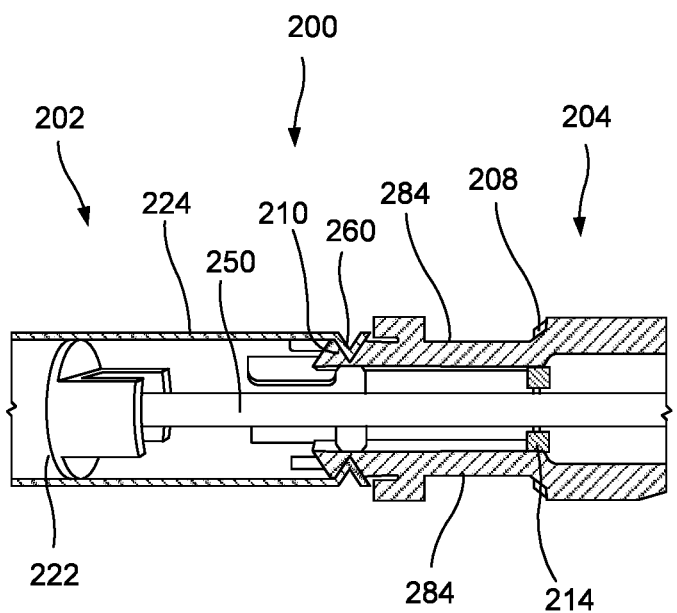
FIG. 16 shows a longitudinal cross-sectional view of the clip assembly and the applicator of the system of FIG. 13, in the coupled configuration.

In this embodiment, the releasing structure 214 may be configured as a protrusion extending inward toward the longitudinal axis of the locking sleeve 208 such that, when an enlarged end 248 of the control member 250 is disengaged from the yoke 222 upon locking of the clip assembly 202 in a tissue clipping configuration, the control member 250 may be drawn further proximally until the enlarged end 248 contacts the protrusion. The protrusion may extend from a portion of the deflectable tab 284 so that, when the enlarged end 248 is pressed proximally against the releasing structure 214, the proximal force against the releasing structure 214 causes the deflectable tab 284 to be moved inward, thereby releasing the bend 260 of the capsule 224 from the window of the engaging structure 210. The control member 250 is drawn proximally until the locking sleeve 208 is entirely disconnected from the capsule 224, releasing the clip assembly 202 from the applicator 204. As shown in FIGS. 14 and 16, the locking sleeve 208 may include a pair of deflectable tabs 284 diametrically opposing one another so that protrusions of the releasing structure 214 extend from each of the deflectable tabs 284.

Although the releasing structure 214 is described and shown as a protrusion in this embodiment, the releasing structure may have any of a variety of configurations. For example, in another embodiment, as shown in FIGS. 17-18, a releasing structure 214' may also be configured as an element extending across a channel 215' of a locking sleeve 208' between deflectable tabs 284' thereof. The element may include an opening extending therethrough, the opening sized and shaped to slidably receive a length of a control wire 250' of an applicator 204' while preventing the enlarged end 248' of the control wire 250' from being passed therethrough. The enlarged end 248' is positioned distally of the releasing structure 214' so that, when it is desired to release a clip assembly 202' from the applicator 204', the control wire 250' is moved proximally until the enlarged head 248' contacts the element of the releasing structure 214'. Similarly to the releasing structure 214 described above, a proximal force of the enlarged head 248' against the releasing structure 214' causes the deflectable tabs 284' to be moved inward toward one another, out of engagement with a capsule 224'. The element of the releasing structure 214' of this embodiment may be shaped (e.g., angled or curved) to include a seat sized and shaped for engaging the enlarged head 248'. The releasing structure 214', however, may have ant of a variety of configurations so long as the releasing structure 214' is sized and shaped to interface with the enlarged end 248' to move the deflectable tabs 284' inward toward one another.

Although the capsule 224 is described and shown as including the bend 260 for engaging the engaging structure 210 configured as a window, it will be understood by those of skill in the art that the capsule 224 and the locking sleeve 208 may include any of a variety of corresponding engaging features for releasably coupling to one another. For example, in another embodiment, the capsule 224 may include an engaging window substantially similar to the engaging window 160 of the capsule 224, and the engaging structure 210 of the locking sleeve 208 may be configured as a bend or other protrusion extending outward, away from the longitudinal axis thereof. These corresponding engaging features may be coupled to one another in a manner substantially similar to the method described above. It will be understood by those of skill in the art that the system 200 may be used in a manner substantially similar to the system 100.

Figure 19:
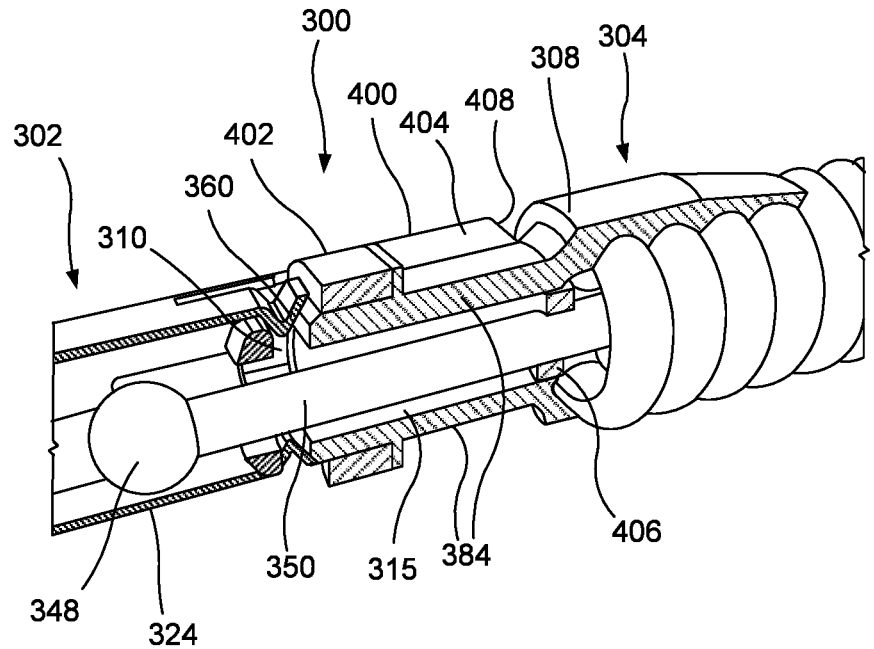
FIG. 19 shows a cross-sectional perspective view of a system according to another exemplary embodiment of the present disclosure.
Figure 20:
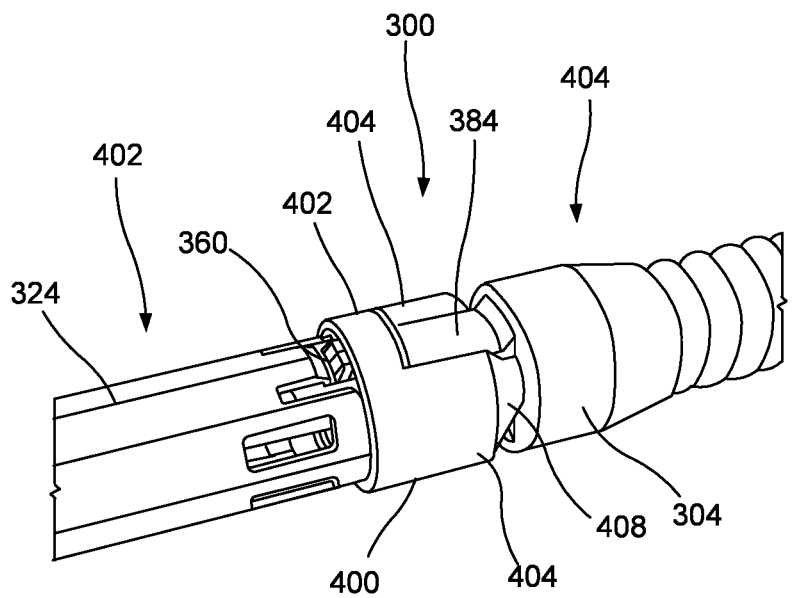
FIG. 20 shows a perspective view of the system of FIG. 19.

As shown in FIGS. 19-20, a system 300 may be substantially similar to the systems 100, 200, described above, comprising a clip assembly 302 loadable onto an applicator 304 via a locking sleeve 308 at a distal end thereof. The locking sleeve 308 may be substantially similar to the locking sleeve 208, described above with respect to the system 200, including deflectable tabs 384 which may be received within a capsule 324 of the clip assembly 302 to be engaged therewith. In particular, a distal portion of the deflectable tabs 384 including engaging structures 310 may be received within the capsule 324 to engage corresponding engaging structures 360 thereof. The system 300, however, further comprises an outer sleeve 400 extending about a portion of the deflectable tabs 384 and including a release structure which, when engaged by an enlarged end 348 of a control member 350 of the applicator 304, moves the deflectable tabs 384 out of engagement with the capsule 324 to deploy the clip assembly 302 in a body gripped over target tissue.

In particular, the outer sleeve 400 includes a first portion 402 extending about a portion of the deflectable tabs 384 immediately proximal an engaging structure 310 (e.g., windows) of the deflectable tabs 384 and a second portion 404 extending proximally from the first portion 402. The first portion 402 may be configured as a ring extending about a portion of the deflectable tabs 384 while the second portion 404 may be configured as a pair of arms extending proximally therefrom. The pair of arms 404 may be diametrically opposed to one another and offset with respect to the deflectable tabs 384 so that release tabs 406 at proximal ends 408 of the arms 404 extend into a channel 315 of the locking sleeve 308 between proximal ends 385 of the deflectable tabs 384. The release tabs 406 extend laterally inward from the proximal ends 408 of the arms 404 and into the channel 315 to be engaged by an enlarged end 348 of a control member 350 of the applicator 304. In one embodiment, the release tabs 406 of each of the arms 404 may be separated from one another substantially similarly to the releasing structure 214 of system 200. In another embodiment, the release tabs 406 may be integrally formed with one another so that the release tabs 406 may form a single element extending across the channel 315, substantially similarly to the releasing structure 214'.

When it is desired to deploy the clip assembly 302, the control member 350 is disengaged from clip arms 318 of the clip assembly 302, substantially as described above with respect to system 100, and drawn proximally into the locking sleeve 308 until the enlarged end 348 comes into contact with the release tabs 406. A proximal force on the release tabs 406 via the enlarged end 448 causes the first portion 402 (e.g., ring portion) of the outer sleeve 400 to deform. The deformed first portion 402 presses against the deflectable tabs 384, moving the deflectable tabs 384 toward one another and out of engagement with the capsule 324. The applicator 404 may then be withdrawn, leaving the clip assembly 302 in the body.

It will be apparent to those skilled in the art that various modifications may be made in the present disclosure, without departing from the scope of the disclosure.

What is claimed is:

1. A method for treating tissue, comprising:
    loading a first clip assembly on an applicator by coupling a control member of the applicator to a yoke connecting proximal ends of clip arms of the first clip assembly by pushing an enlarged distal end of the control member into a socket of the yoke, and by coupling a locking sleeve of the applicator to a capsule of the first clip assembly by pushing the locking sleeve distally along the proximal end of the capsule, a deflectable tab of the locking sleeve deflecting such that an engaging structure of the deflectable tab rides along a surface of the capsule until the engaging structure engages a corresponding engaging structure of the capsule;
    inserting the loaded clip assembly into a target site within a living body via a working channel of an endoscope;
    moving the first clip assembly between a tissue receiving configuration, in which distal ends of the clip arms are separated from one another, and a tissue clipping configuration, in which distal ends of the clip arms are moved toward one another, by moving the control member longitudinally relative to the locking sleeve until a target tissue is gripped therebetween, as desired; and
    releasing the first clip assembly from the applicator by drawing the control member proximally relative to the yoke, beyond a predetermined threshold value, so that the control member disengages from the yoke and a portion of the control member engages a releasing structure positioned proximally of the engaging structure of the deflectable tab, engagement of the portion of the control member and the releasing structure causing the deflectable tab to deflect and disengage the engaging structure of the deflectable tab from the corresponding engaging structure of the capsule.

2. The method of claim 1, further comprising locking the first clip assembly in the tissue clipping configuration such that the target tissue is locked between the clip arms.

3. The method of claim 2, wherein locking the first clip assembly in the tissue clipping configuration comprises a locking tab at the proximal end of at least one of the clip arms engaging a locking window extending through a wall of the capsule.

4. The method of claim 1, further comprising inserting a distal portion of the applicator through an opening of a cartridge housing the first clip assembly to load the first clip assembly to the applicator.

5. The method of claim 1, further comprising loading a second clip assembly to the applicator by coupling the control member to a yoke of the second clip assembly and by coupling the locking sleeve to a proximal end of a capsule of the second clip assembly.

6. The method of claim 1, wherein each of the engaging structure of the deflectable tab and the releasing structure is a bend extending into a channel of the locking sleeve, the locking sleeve mountable over the proximal end of the capsule and the deflectable tab deflectable radially outward away from a longitudinal axis of the locking sleeve to releasably load the first clip assembly on the applicator.

7. The method of claim 1, wherein the first clip assembly includes a stop washer slidably mounted over the portion of the control member, a surface of the stop washer engaging the releasing structure to deflect the deflectable tab.

8. The method of claim 1, wherein the engaging structure of the deflectable tab is a window extending laterally through the deflectable tab and the corresponding engaging structure of the capsule is a bend extending outward, away from a longitudinal axis of the capsule so that the locking sleeve is receivable within a channel of the capsule and the deflectable tab is deflectable radially inward toward a longitudinal axis of the locking sleeve.

9. The method of claim 8, wherein the releasing structure is a protrusion extending inward into a channel of the locking sleeve so that, when the portion of the control member engages the protrusion, the deflectable tab deflects radially inward toward the longitudinal axis of the locking sleeve.

10. The method of claim 8, wherein the releasing structure is an element extending across a channel of the locking sleeve from an interior surface of the deflectable tab so that, when the portion of the control member engages the releasing structure, the deflectable tab deflects radially inward toward the longitudinal axis of the locking sleeve.

11. The method of claim 1, wherein the releasing structure is a first portion of an outer sleeve, the outer sleeve extending about a portion of the deflectable tab proximal of the engaging structure of the deflectable tab and having a second portion, the second portion extending proximally from the first portion.

12. The method of claim 11, wherein the second portion of the outer sleeve includes an arm offset with respect to the deflectable tab, the arm including a release tab at a proximal end thereof extending laterally inward into a longitudinal channel of the locking sleeve so that, when the portion of the control member engages the release tab, the release tab applies a proximal force on the first portion deforming the first portion, the deformed first portion deflecting the deflectable tab radially inward toward the longitudinal axis of the locking sleeve.

13. The method of claim 1, wherein the clip an us are biased in the tissue receiving configuration.

* * * * *